(12) United States Patent
Navarro

(10) Patent No.: US 7,193,220 B1
(45) Date of Patent: Mar. 20, 2007

(54) MODULAR RADIATION BEAN ANALYZER

(76) Inventor: Daniel Navarro, 601 NE. Emerson St., Port St. Lucie, FL (US) 34983

( * ) Notice: Subject to any disclaimer, the term of this patent is extended or adjusted under 35 U.S.C. 154(b) by 0 days.

(21) Appl. No.: 11/427,197

(22) Filed: Jun. 28, 2006

(51) Int. Cl.
*G01N 23/00* (2006.01)
(52) U.S. Cl. .................... 250/374; 378/207; 250/252.1
(58) Field of Classification Search ................ 250/374, 250/252.1; 378/207
See application file for complete search history.

(56) References Cited

U.S. PATENT DOCUMENTS

| | | | |
|---|---|---|---|
| 4,988,866 A | 1/1991 | Westerlund | |
| 5,006,714 A | 4/1991 | Attix | |
| 5,621,214 A | 4/1997 | Sofield | |
| 5,627,367 A | 5/1997 | Sofield | |
| 5,635,709 A * | 6/1997 | Sliski et al. ............. | 250/252.1 |
| 6,225,622 B1 | 5/2001 | Navarro | |
| 2005/0173648 A1 | 8/2005 | Schmidt et al. | |
| 2006/0033044 A1 | 2/2006 | Gentry et al. | |

* cited by examiner

*Primary Examiner*—David Porta
*Assistant Examiner*—Mark R. Gaworecki
(74) *Attorney, Agent, or Firm*—McHale & Slavin, P.A.

(57) ABSTRACT

The instant invention is a modular radiation beam analyzer for measuring the distribution and intensity of radiation produced by a radiation source. More specifically, the instant invention is a modular radiation scanning device that includes up to three modules. By selecting and assembling a predetermined number of modules a radiation detector may be manipulated through up to three axes for radiation beam scans as well as direct Tissue Maximum Ratio (TMR) and/or Tissue Phantom Ratio (TPR) scans.

22 Claims, 17 Drawing Sheets

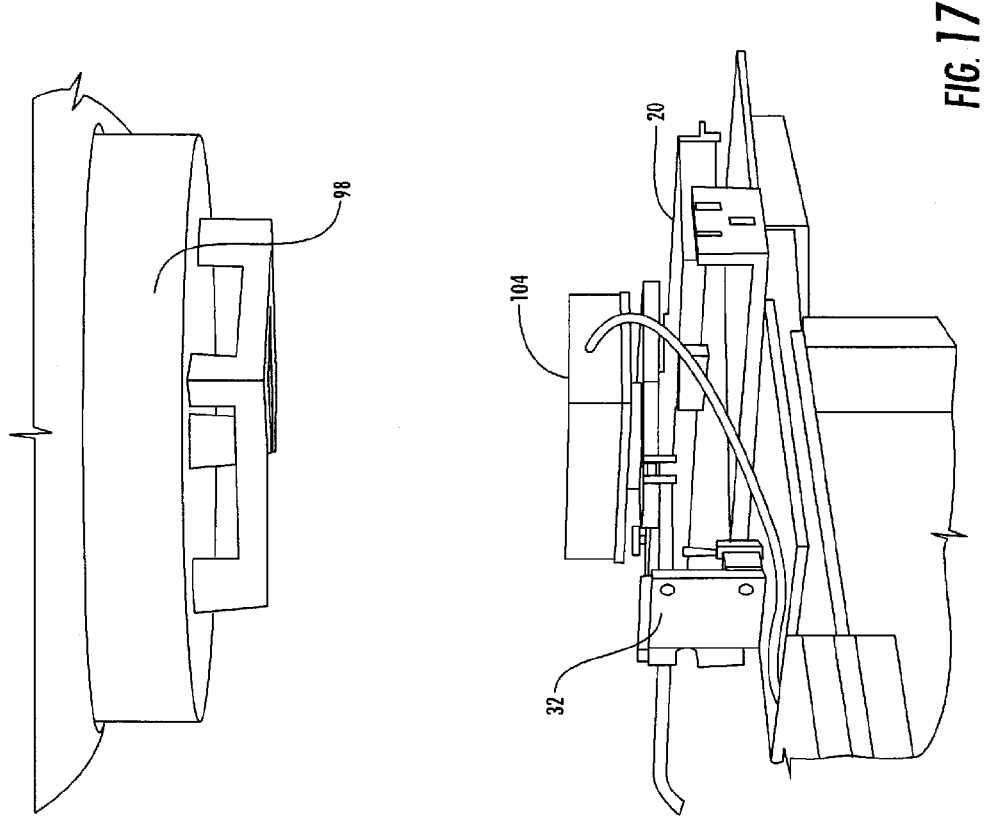

MODULAR RADIATION BEAN ANALYZER

FIELD OF THE INVENTION

This invention relates to a method and device for measuring the radiation dose of a linear accelerator or other radiation producing device at the target, and particularly relates to the use of a movable radiation detector, usually an ion chamber.

BACKGROUND OF THE INVENTION

Various well-known medical techniques for the treatment of malignancies involve the use of radiation. Radiation sources, for example medical linear accelerators, are typically used to generate radiation to a specific target area of a patient's body. Use of appropriate dosimetry insures the application of proper doses of radiation to the malignant areas and is of utmost importance. When applied, the radiation produces an ionizing effect on the malignant tissue, thereby destroying the malignant cells. So long as the dosimetry of applied radiation is properly monitored, the malignancy may be treated without detriment to the surrounding healthy tissue. Accelerators may be utilized, each of which have varying characteristics and output levels. The most common type of accelerator produces pulse radiation, wherein the output has the shape of a rectangular beam with a cross-sectional area which is typically between 16 and 1600 square centimeters. Rectangular or square shapes are often changed to any desired shape using molded or cast lead or cerrobend materials. More advanced accelerators use multi-leaf collimators. Other accelerators are continuous or non-pulsed such as cobalt radiation machines; and accelerators that utilize a swept electron beam, which sweep a very narrow electron beam across the treatment field by means of varying electromagnetic fields.

To ensure proper dosimetry, linear accelerators used for the treatment of malignancies must be calibrated. Both the electron and photon radiation must be appropriately measured and correlated to the particular device. The skilled practitioner must insure that both the intensity and duration of the radiation treatment is carefully calculated and administered so as to produce the therapeutic result desired while maintaining the safety of the patient. Parameters such as flatness, symmetry, radiation and light field alignment are typically determined. The use of too much radiation may, in fact, cause side effects and allow destructive effects to occur to the surrounding tissue. Use of an insufficient amount of radiation will not deliver a dose that is effective to eradicate the malignancy. Thus, it is important to be able to determine the exact amount of radiation that will be produced by a particular machine and the manner in which that radiation will be distributed within the patient's body.

In order to produce an accurate assessment of the radiation received by the patient, at the target area, some type of pattern or map of the radiation at varying positions within the patient's body must be produced. These profiles correlate 1) the variation of dose with depth in water generating percent depth dose profiles and 2) the variation of dose across a plane perpendicular to the radiation source generating the cross beam profiles. These particular measurements of cross beam profiles are of particular concern in the present invention. Although useful for other analyses, the variation of the beam uniformity within the three dimensional radiation field is the main purpose of this device.

There are companies that provide the calibration service to hospitals and treatment centers. These technicians must visit the facility and conduct the calibration of the radiation source with their own equipment. This requires lightweight, easily portable, less cumbersome radiation measuring devices that can be quickly assembled and disassembled on site. The actual scanning should also be expeditious with the results available within a short time frame. Such equipment allows a technician to be more efficient and calibrate more radiation devices in a shorter period of time.

One existing system for measuring the radiation that is produced by medical linear accelerators utilizes a large tank on the order of 50×50×50 cm filled with water. A group of computer controlled motors move the radiation detector through a series of pre-programmed steps along a single axis beneath the water's surface. Since the density of the human body closely approximates that of water, the water-filled tank provides an appropriate medium for creating a simulation of both the distribution and the intensity of radiation which would likely occur within the patient's body. The aforementioned tank is commonly referred to as a water phantom. The radiation produced by the linear accelerator will be directed into the water in the phantom tank, at which point the intensity of the radiation at varying depths and positions within the water can be measured with the radiation detector. As the radiation penetrates the water, the direct or primary beam is scattered by the water, in much the same way as a radiation beam impinging upon the human patient. Both the scattered radiation as well as the primary radiation are detected by the ion-chamber, which is part of the radiation detector.

The ion-chamber is essentially an open air capacitor which produces an electrical current that corresponds to the number of ions produced within its volume. The detector is lowered to a measurement point within the phantom tank and measurements are taken over a particular time period. The detector can then be moved to another measurement point where measurements are taken as the detector is held in the second position. At each measuring point a statistically significant number of samples are taken while the detector is held stationary.

DESCRIPTION OF THE PRIOR ART

Several prior art devices are known to teach systems for ascertaining the suitable dosimetry of a particular accelerator along with methods for their use.

U.S. Pat. Nos. 5,621,214 and 5,627,367, to Sofield, are directed to a radiation beam scanner system which employs a peak detection methodology. The device includes a single axis mounted within a water phantom. In use, the water phantom must be leveled and a reference detector remains stationary at some point within the beam while the signal detector is moved up and down along the single axis by the use of electrical stepper motors.

While these devices employ a water phantom, they are limited to moving the signal detector along the single axis and can only provide a planar scan of the beam.

U.S. Patent Application Publication 2006/0033044 A1, to Gentry et al., is directed to a treatment planning tool for multi-energy electron beam radiotherapy. The system consists of a stand-alone calculator that enables multi-energy electron beam treatments with standard single electron beam radio-therapy equipment thereby providing improved dose profiles. By employing user defined depth-dose profiles, the calculator may work with a wide variety of existing standard electron beam radiotherapy systems.

U.S. Pat. No. 6,225,622, issued May 1, 2001 to Navarro, the inventor here, describes a dynamic radiation measuring device that moves the ion chamber through a stationary radiation beam to gather readings of radiation intensity at various points within the area of the beam. The disclosure of this patent is incorporated herein, by reference.

U.S. Pat. No. 4,988,866, issued Jan. 29, 1991, to Westerlund, is directed toward a measuring device for checking radiation fields from treatment machines used for radiotherapy. This device comprises a measuring block that contains radiation detectors arranged beneath a cover plate, and is provided with field marking lines and an energy filter. The detectors are connected to a read-out unit for signal processing and presentation of measurement values. The dose monitoring calibration detectors are fixed in a particular geometric pattern to determine homogeneity of the radiation field. In use, the measuring device is able to simultaneously check the totality of radiation emitted by a single source of radiation at stationary positions within the measuring block.

U.S. Patent Application Publication 2005/0173648 A1, to Schmidt et al., is directed to a wire free, dual mode calibration instrument for high energy therapeutic radiation. The apparatus includes a housing with opposed first and second faces holding a set of detectors between the first and second faces. A first calibrating material for electrons is positioned to intercept electrons passing through the first face to the detectors, and a second calibrating material for photons is positioned to intercept photons passing through the second face to those detectors.

These devices do not use a water phantom and are additionally limited in that all of the ionization detectors are in one plane. This does not yield an appropriate three-dimensional assessment of the combination of scattering and direct radiation which would normally impinge the human body undergoing radiation treatment. Thus, accurate dosimetry in a real-life scenario could not be readily ascertained by the use of these devices.

U.S. Pat. No. 5,006,714, issued Apr. 9, 1991, to Attix utilizes a particular type of scintillator dosimetry probe which does not measure radiation directly but instead measures the proportional light output of a radiation source. The probe is set into a polymer material that approximates water or muscle tissue in atomic number and electron density. Attix indicates that the use of such a detector minimizes perturbations in a phantom water tank.

Additionally, there is an apparatus called a Wellhofer bottle-ship which utilizes a smaller volume of water than the conventional water phantom. The Wellhofer device utilizes a timing belt and motor combination to move the detector through the water, thus requiring a long initial set-up time.

Thus, there exists a need for a modular radiation beam analyzer device. The device should be portable and capable of being quickly assembled for use and disassembled for transport. The device should also be capable of repeated, accurate detection of both scattering and direct radiation components from radiation devices along at least two, and more preferably three, axes for three dimensional scans of radiation beams.

SUMMARY OF THE INVENTION

The instant invention is a modular radiation beam analyzer for measuring the distribution and intensity of radiation produced by a radiation source. More specifically, the instant invention is a modular radiation scanning device that is capable of moving a radiation detector through up to three axes for precision three dimensional radiation beam scans.

The present invention is based upon the general principle of scanning a simulated target area of radiation by the use of a radiation detector attached to a moving modular platform to develop a one, two or three dimensional plot of the dosage delivered.

The modular apparatus of this invention may be used in a water phantom or with solid water slabs or wafers simulating that portion of the target area which affects the radiation beam. Therefore, the water phantom may be mobile or immobile with the dynamic detector moving through the phantom or moving through the radiation beam carrying the phantom.

In one embodiment, the modular platform translates the detector in a water phantom. The use of the water phantom results in the scattering of the directly applied radiation in the water tank in a manner similar to that which occurs when this direct radiation impinges upon the human body being treated.

One characteristic of the invention is the over-all speed of the process of producing a plot of radiation dosage; eg., this modular apparatus may be assembled and disassembled in less than 5 minutes. Each axis is constructed and arranged for attachment to an orthogonal axis with thumb screws for ease and speed of assembly. All three axes may be leveled manually using only two leveling screws. Alternatively, the device may be leveled electronically, whereby the computer will move the radiation detector parallel to the surface of the water within the phantom tank.

The controller utilized with the instant invention permits incremental and/or continuous movement of the radiation detector. In addition, the controller permits up to about 42000 samples to be taken for every "step" of movement. The size of the step can be changed electronically from 0.01 millimeter to 1 millimeter depending upon the accuracy desired. The device may be operated manually, via a hand control, or alternatively the controller may include a computer whereby the field of scan may be pre-programmed. Thereafter, the scan will be completed automatically.

Accordingly, it is a primary objective of the instant invention to provide a portable and easily assembled modular apparatus for radiation detection and measurement which utilizes rapid and accurate setup and significantly reduces the measurement time required by traditionally used scanning systems.

It is another objective of the instant invention to provide a modular radiation measuring device including up to three axes, each including electrically powered motors and lead screws.

It is yet another objective of the instant invention to provide a platform having two leveling points to level the axes of the apparatus with respect to the water surface within the water phantom tank.

It is a further objective of the instant invention to provide a system and method for electronically leveling the movements of the device.

It is yet a further objective of the instant invention to provide a system and method for traversing a dynamic phantom through a radiation beam for radiation measurement.

It is still yet a further objective of the instant invention to provide a water phantom of unique shape for direct measurement of radiation.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 17 is a perspective view illustrating the X-axis and the Z-axis being used in combination with a dynamic phantom.

DETAILED DESCRIPTION OF THE INVENTION

Figure 1:
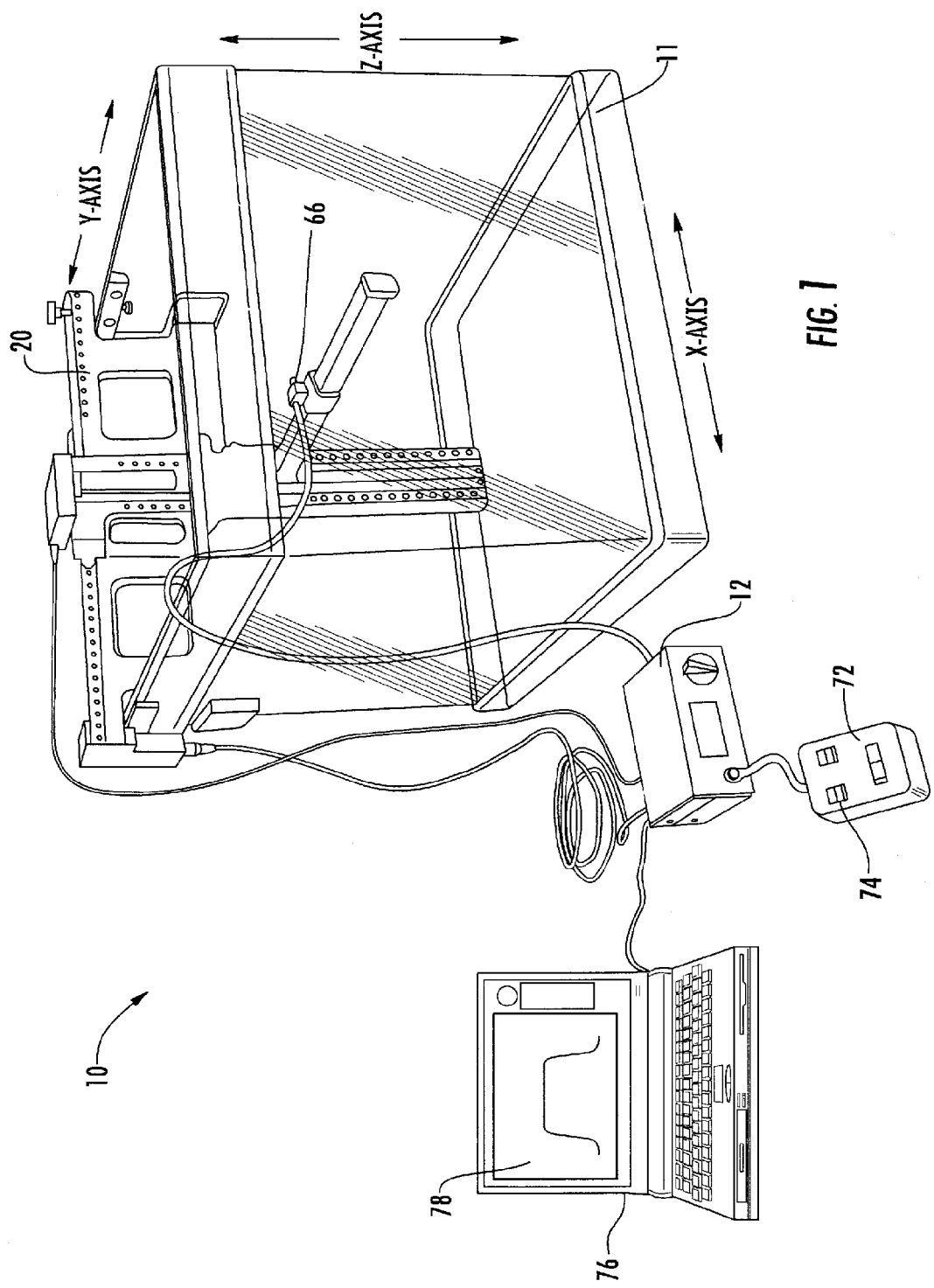
FIG. 1 is a top perspective view of one embodiment of the instant invention.
Figure 2:
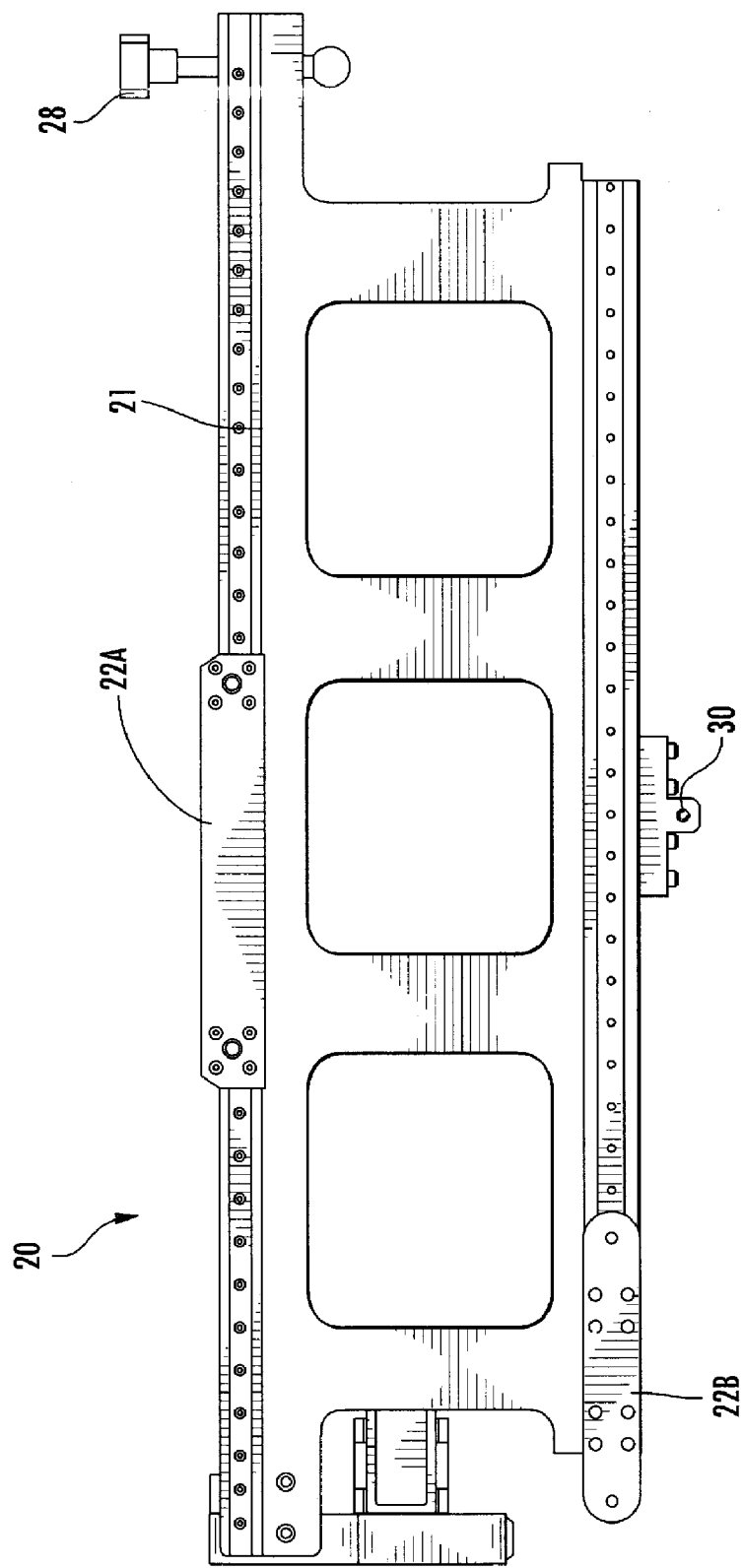
FIG. 2 is a front view of one embodiment of the X-axis guideway of the instant invention.
Figure 3:
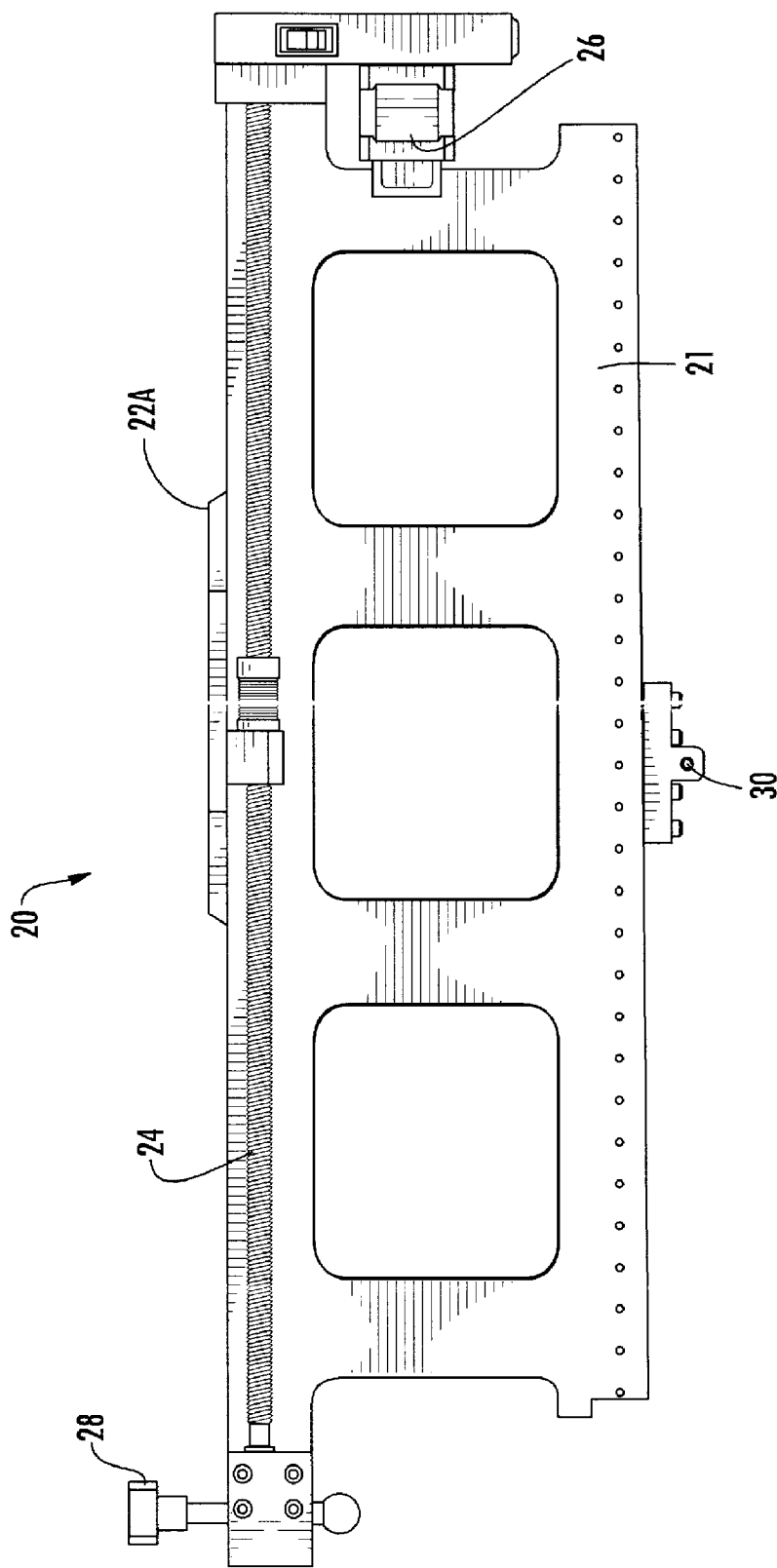
FIG. 3 is a back view of one embodiment of the X-axis guideway of the instant invention.
Figure 4:
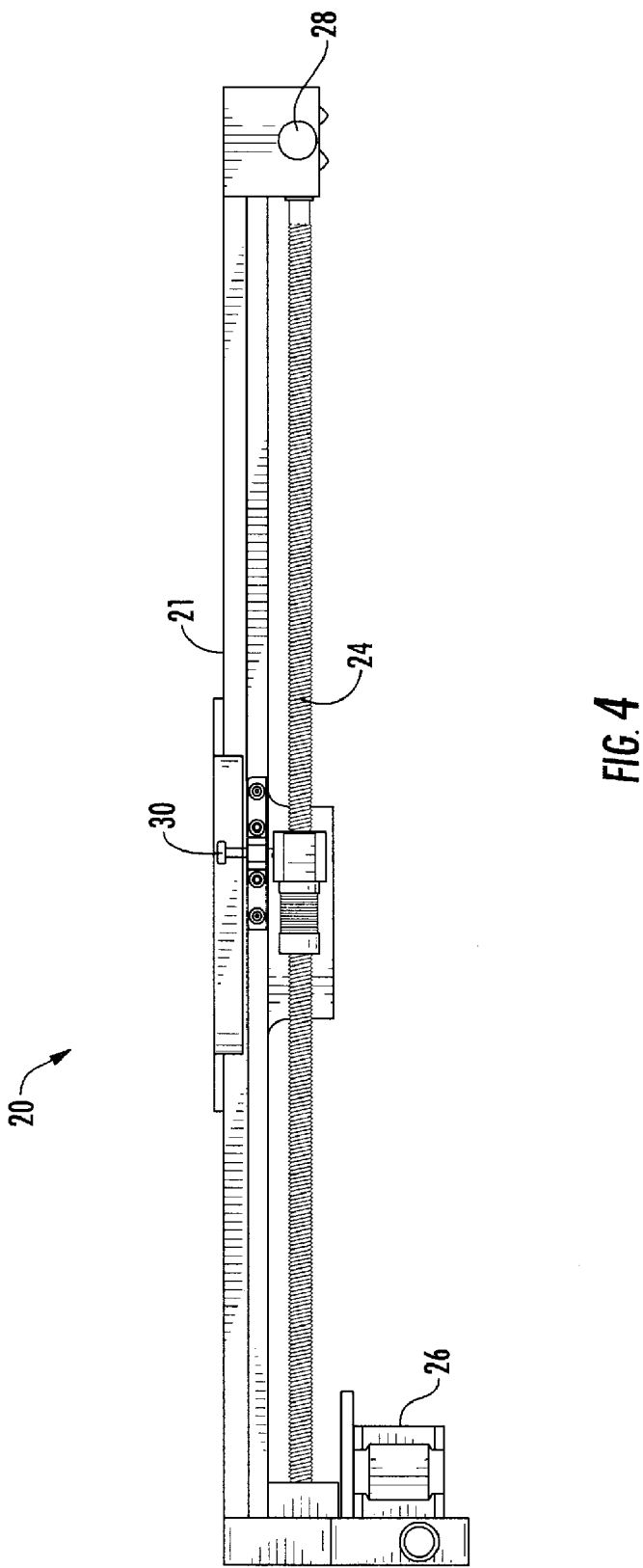
FIG. 4 is a bottom view of one embodiment of the X-axis guideway of the instant invention.
Figure 5:
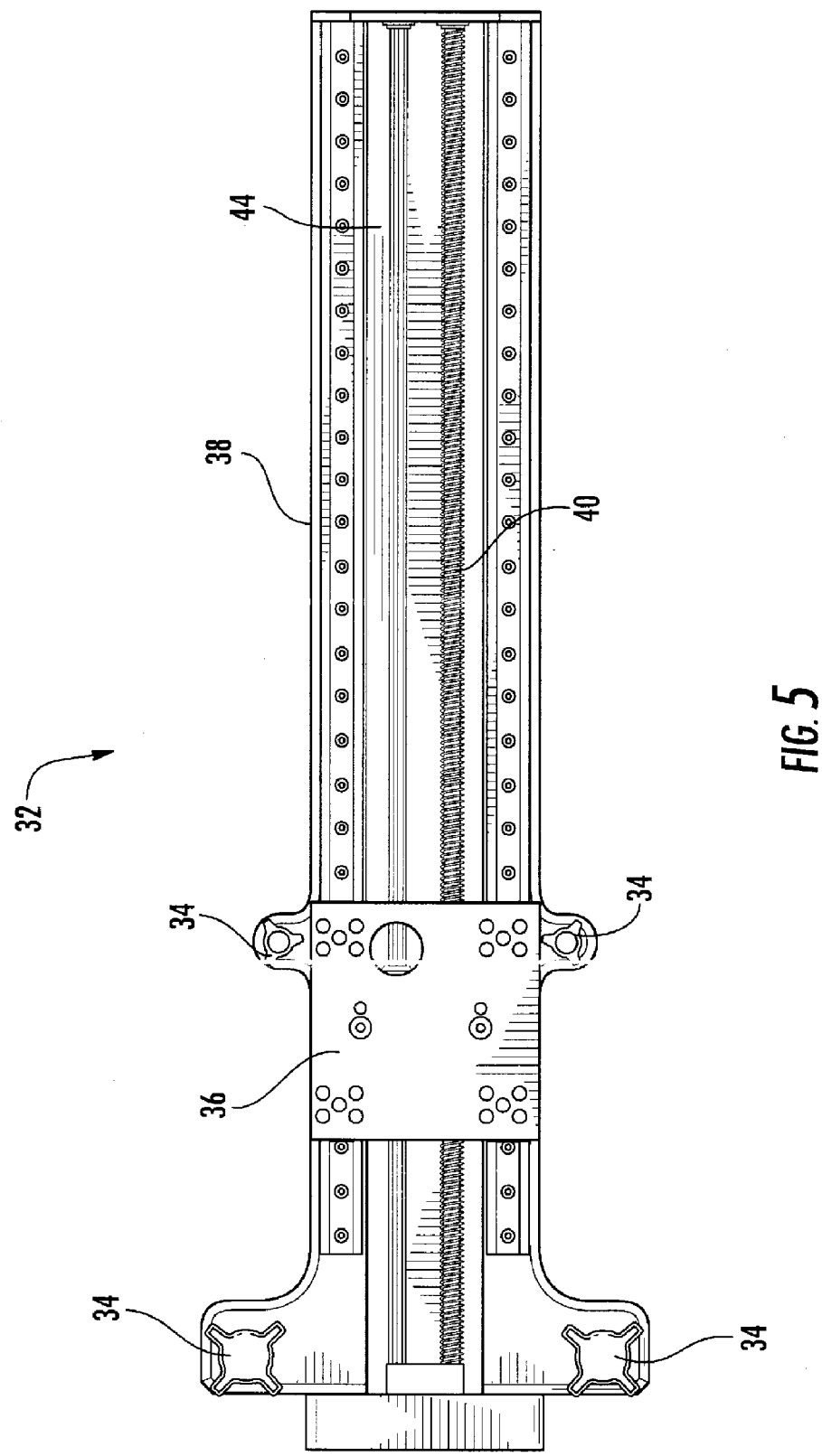
FIG. 5 is a front view of one embodiment of the Z-axis guideway of the instant invention.
Figure 6:
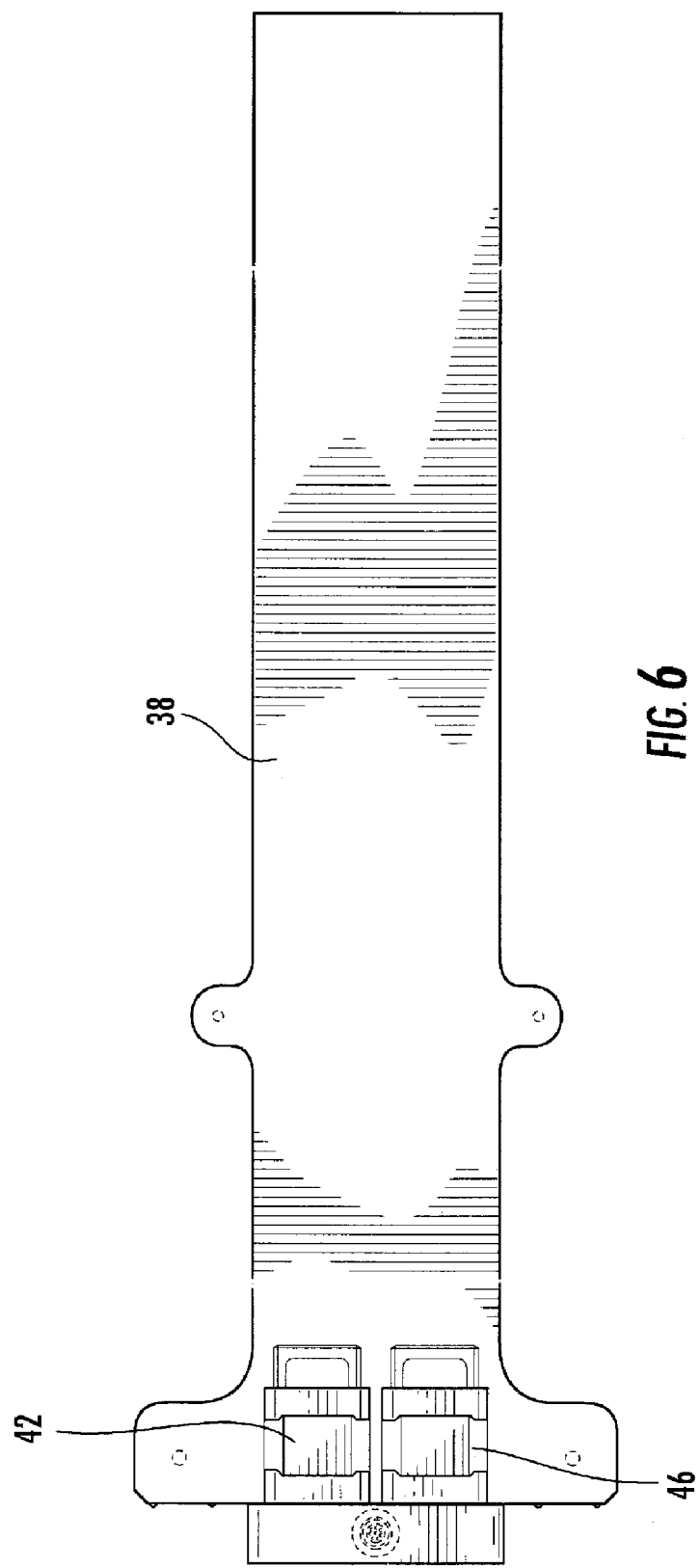
FIG. 6 is a rear view of one embodiment of the Z-axis guideway of the instant invention.
Figure 7:
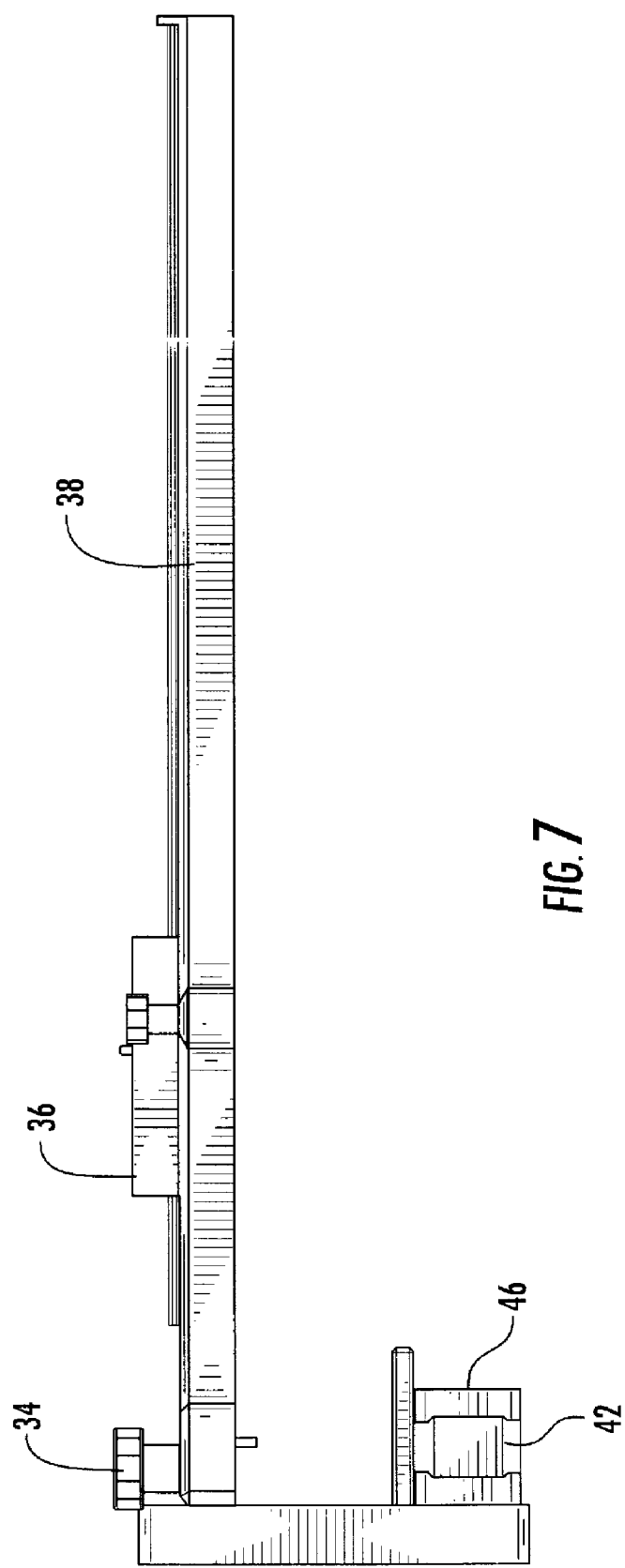
FIG. 7 is a left side view of one embodiment of the Z-axis guideway of the instant invention.
Figure 8:
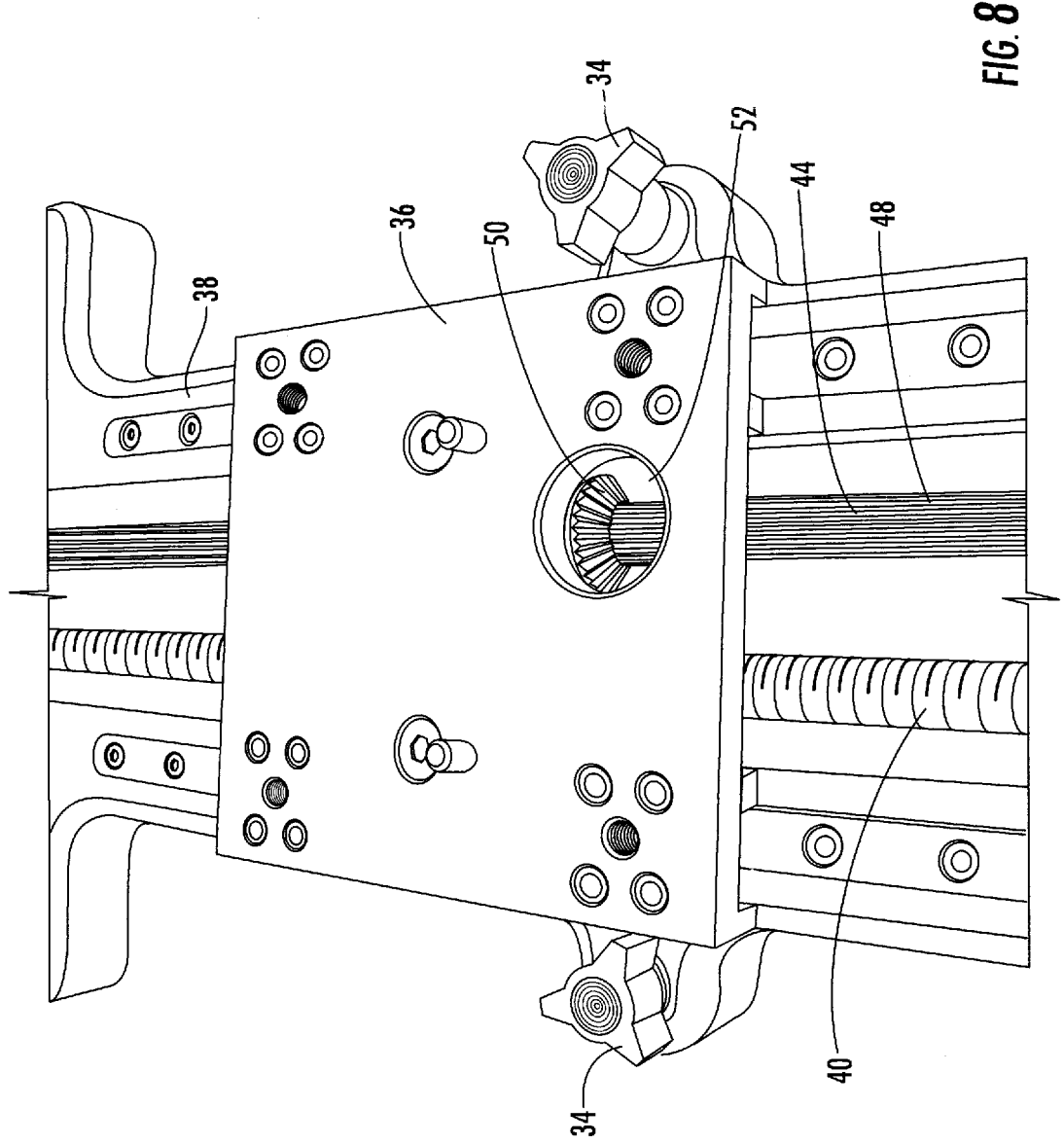
FIG. 8 is a partial perspective view of one embodiment of the Z-axis guideway of the instant invention, illustrating the carriage, the third lead screw and the line-shaft of the instant invention.
Figure 14:
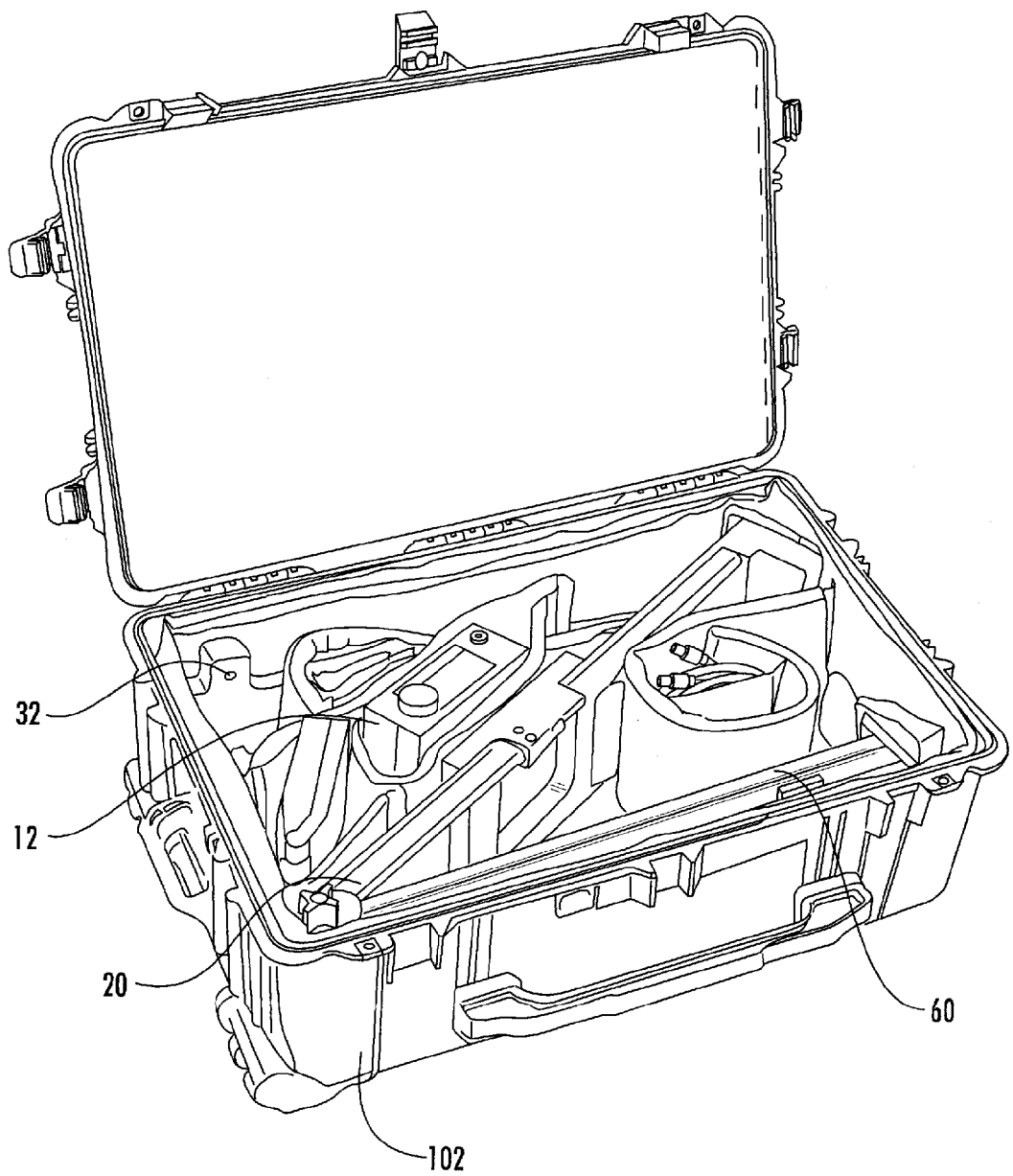
FIG. 14 is a perspective view illustrating the X, Y and Z axes guideways packed into a storage case for ease of transport.

Referring to FIGS. 1 and 14, the modular radiation beam analyzer 10 for measuring the distribution and intensity of radiation produced by a radiation source is illustrated. The radiation beam analyzer 10 generally includes a phantom tank 11 constructed and arranged to contain a material having a density approximating that of a human body. In general, the phantom tank is sized to accommodate an X-axis module 20, a Y-axis module 60 and a Z-axis module 32 of the radiation beam analyzer. The base and walls of the tank may be constructed of acrylic or other suitable material. When filled with water, the tank 11 serves as a water phantom simulating the body of a patient undergoing radiation treatment. The independent X-axis, Y-axis and Z-axis modules are constructed and arranged to fit neatly within a carrying case 102 for ease of transport. Each axis is also constructed and arranged for independent operation with respect to the other axes. In this manner, the desired number of axes may be quickly assembled together at a desired location and radiation measurements may be quickly taken with the predetermined assembly.

Referring to FIGS. 1–4, the X-axis module 20 includes an X-axis guideway 21 (FIGS. 2–4) extending substantially across an upper portion of the phantom tank 11. The X-axis guideway includes an X-axis carriage 22A and 22B slidably secured to the X-axis guideway 21 for controlled movement along the length thereof. In the preferred embodiment, the X-axis guideway 21 includes a first lead screw 24 rotatably mounted thereon. The first lead screw 24 is operably connected to the X-axis carriage 22A to provide linear motion thereto during rotation of the first lead screw. A first stepper motor 26 is operably connected to the first lead screw for controlled bi-directional rotation thereof. In one embodiment the stepper motor is connected to the first lead screw via a geared timing belt (not shown). Alternatively, the stepper motor could be connected to the first lead screw with gears, chains, cables or suitable combinations thereof without departing from the scope of the invention. The first stepper motor 26 is in electrical communication with the controller 12 to provide electrical commands thereto, and if needed to receive feedback from the first stepper motor. Also secured to the X-axis guideway are two leveling screws 28 and 30. Leveling screw 28 cooperates with an upper surface of the tank to provide leveling of all three axes in one plane, while leveling screw 30 cooperates with an inner surface of the tank to provide leveling of all three axes in a second plane. In this manner all three axes may be leveled with only two leveling screws.

Figure 9:
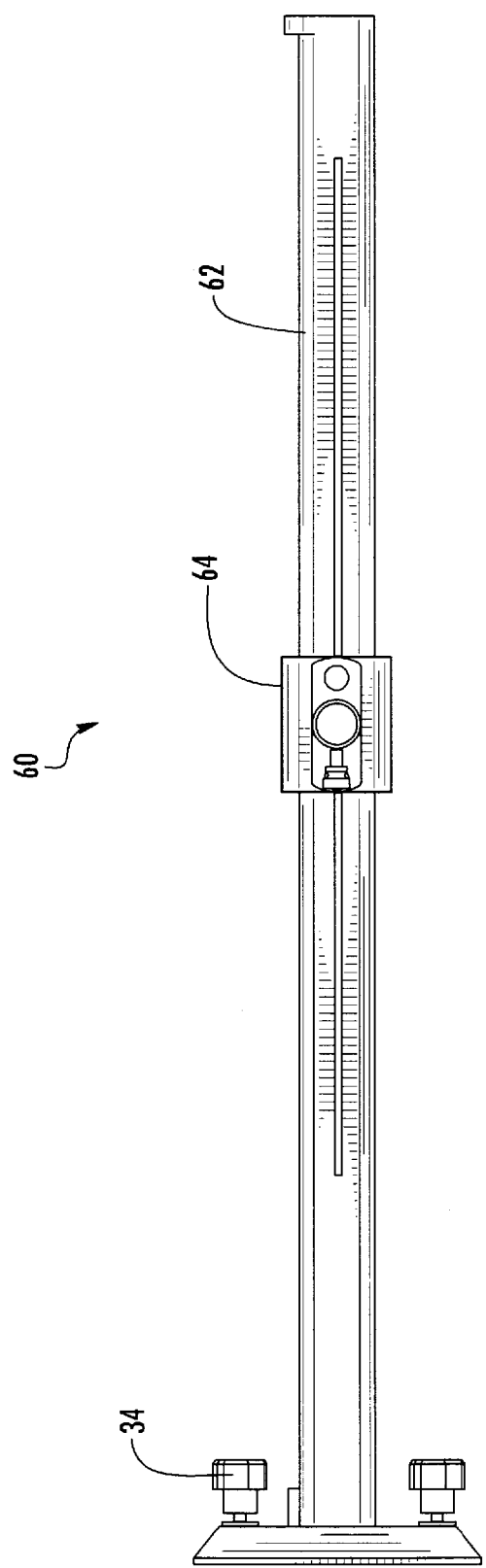
FIG. 9 is a top view of one embodiment of the Y-axis guideway of the instant invention.
Figure 10:
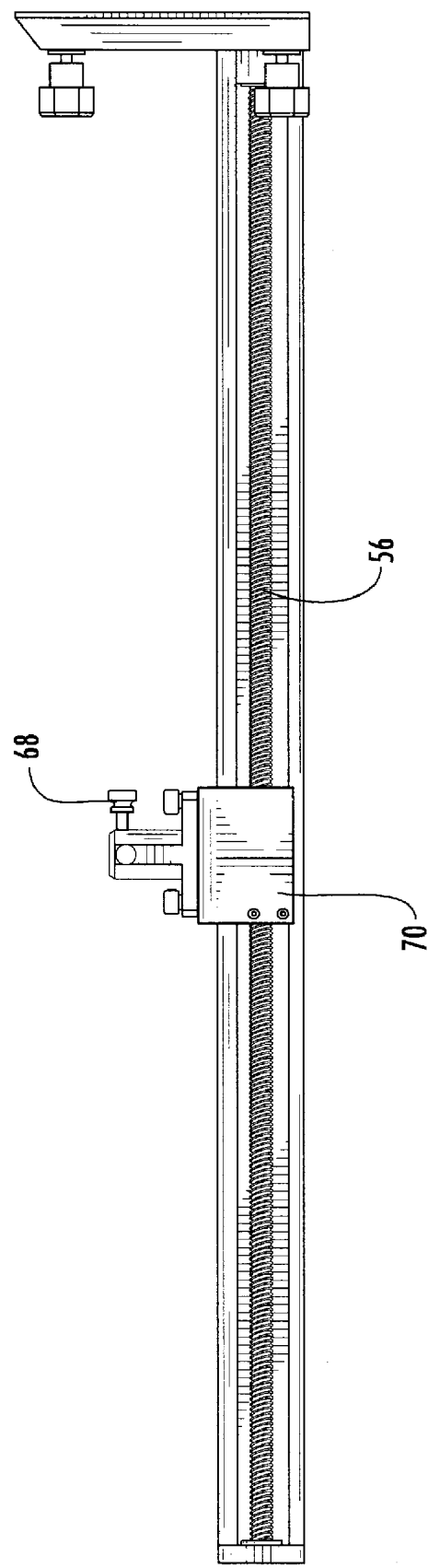
FIG. 10 is right side view of the Y-axis guideway shown in FIG. 9.
Figure 11:
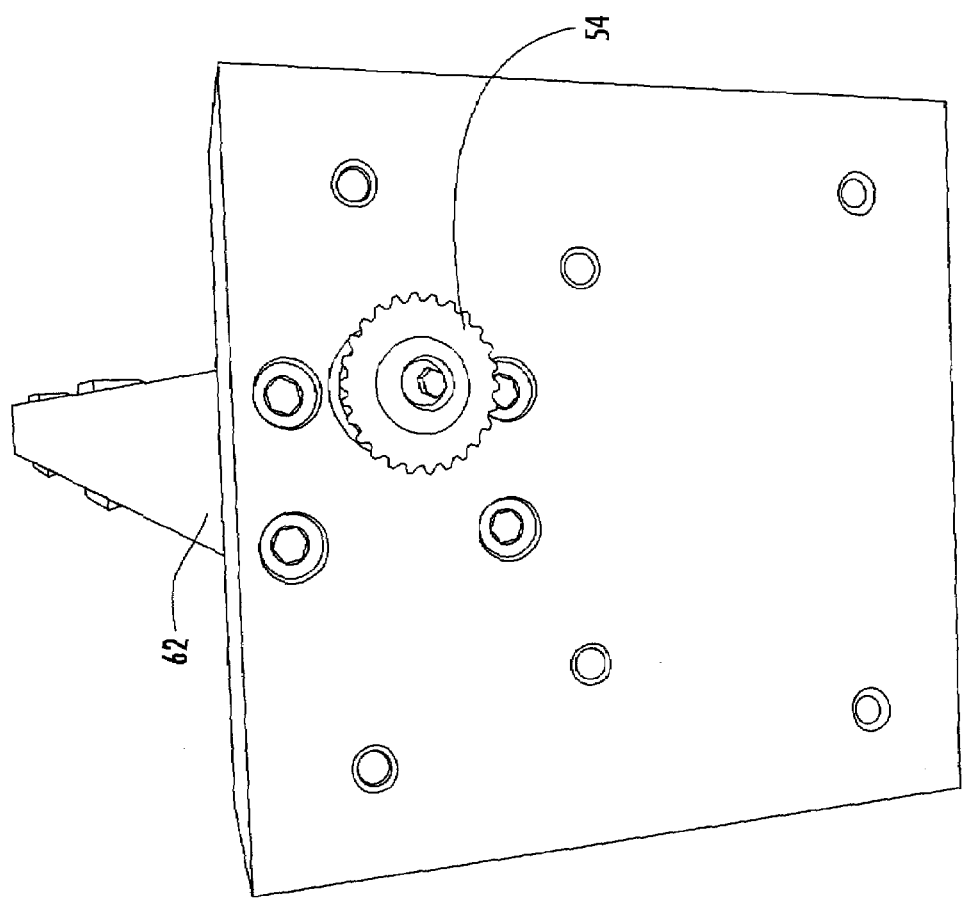
FIG. 11 is an end view of the Y-axis guideway shown in FIG. 9.
Figure 12:
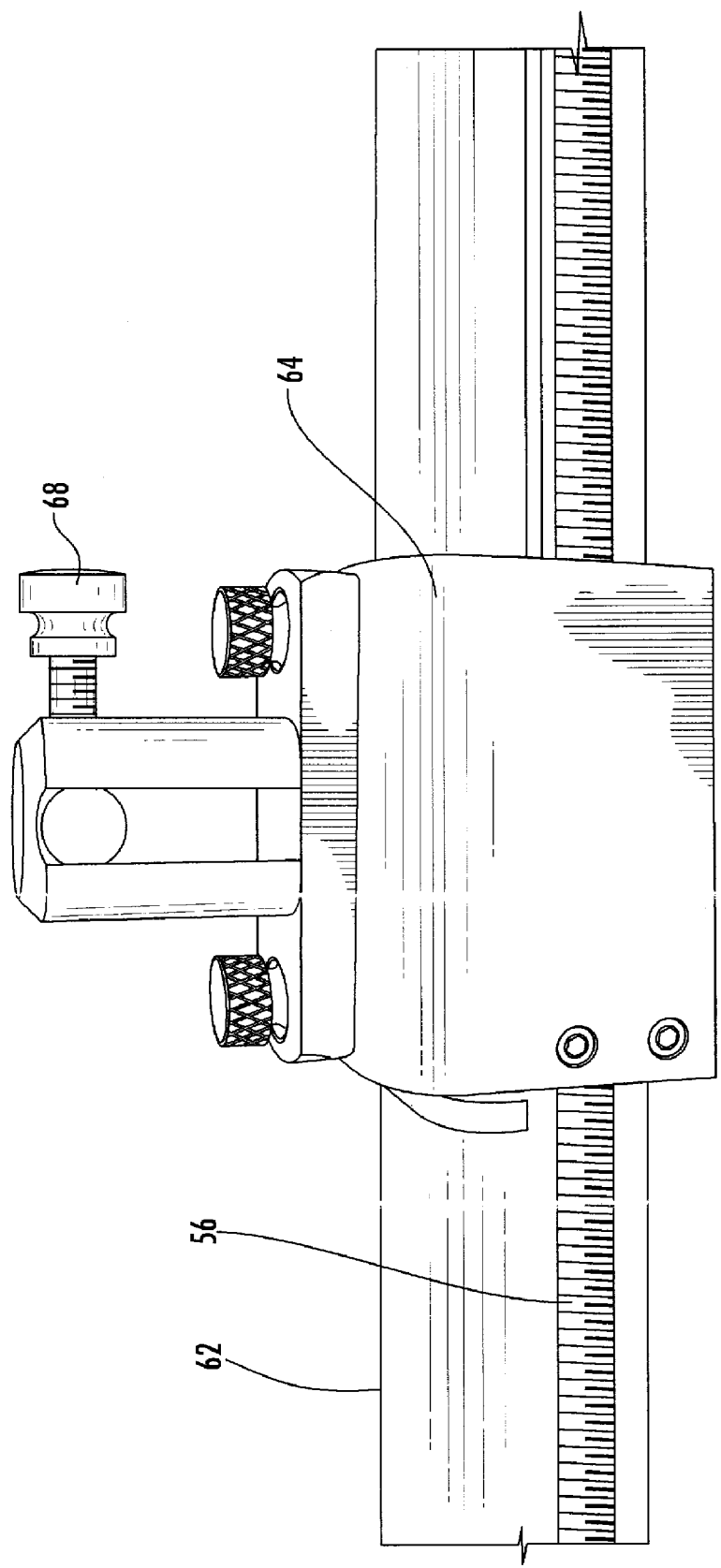
FIG. 12 is a partial perspective view of the Y-axis guideway shown in FIG. 9 illustrating the Y-axis carriage.

Referring to FIGS. 5–8, the Z-axis module 32 is illustrated. The Z-axis module is secured to the X-axis carriage 22A and 22B via thumb screws 34 for movement therewith. A Z-axis carriage 36 is slidably secured to the Z-axis guideway 38 for controlled movement along the length thereof. The Z-axis guideway 38 includes a third lead screw rotatably mounted thereon. The third lead screw 40 is operably connected to the Z-axis carriage 36 to provide linear motion thereto during rotation of the third lead screw. A third stepper motor 42 is operably connected to the third lead screw 40 for controlled bi-directional rotation thereof. In one embodiment the stepper motor 42 is connected to the third lead screw 40 via a geared timing belt (not shown). Alternatively, the stepper motor 42 may be connected to the first lead screw with gears, chains, cables or suitable combinations thereof without departing from the scope of the invention. The third stepper motor 42 is in electrical communication with the controller 12 (FIG. 1) to provide electrical commands thereto and if needed to receive feedback from the third stepper motor 42. The Z-axis guideway also includes a line-shaft 44 rotatably secured thereon. The line-shaft is operably connected to a second stepper motor 46 for selective bi-directional rotation thereof. The second stepper motor is in electrical communication with the controller 12 (FIG. 1). The line-shaft is constructed and arranged to include at least one and more preferably a plurality of splines 48 extending substantially along the length thereof. Slidably mounted on the line shaft is a first beveled gear 50. The beveled gear 50 is secured to the Z-axis carriage 36 so that it moves therewith. The Z-axis carriage is provided with an aperture 52 positioned to allow a second bevel gear 54 (FIG. 11), secured to Y-axis lead screw 56, to engage the first bevel gear 50 when the Y-axis 60 (FIG. 9) is secured to the Z-axis 32. In this manner, the second stepper motor 46 provides rotation to the line-shaft 44 and the same or similar rotation is transferred through the bevel gears to the Y-axis lead screw throughout the motion range of the Z-axis carriage 36 to cause movement of the Y-axis carriage.

Referring to FIGS. 9–12 the Y-axis module 60 is illustrated. The Y-axis module includes a Y-axis guideway 62. The Y-axis guideway is secured to the Z-axis carriage 36, via thumb screws 34, for movement therewith. A Y-axis carriage 64 is slidably secured to the Y-axis guideway 62 for controlled movement along the length thereof. At least one radiation detection probe 66 (FIG. 1) is secured to the Y-axis carriage, via thumb screw 68 for movement therewith. The radiation detection probe is preferably an ion chamber however, it should be noted that other suitable radiation detection probes such as, but not limited to, diodes and the like may be utilized without departing from the scope of the invention. The radiation detection probe is electrically connected to the controller 12, as is well known in the art. The Y-axis guideway 62 includes a second lead screw 56 rotatably mounted thereon. The second lead screw is operably connected to the Y-axis carriage 64 to provide linear motion thereto during rotation of the second lead screw.

Referring to FIGS. 1–12, it should be noted that the X, Y, and Z axes modules are preferably constructed of aluminum having a hard anodized surface for oxidation control, wear properties and appearance. However, it should be noted that other materials well known in the art suitable for construction of the guideways, carriages and lead screws could be utilized without departing from the scope of the invention. Such materials may include, but should not be limited to, metals, plastics, and suitable composites. It should also be noted that while stepper motors are the preferred embodiment for rotation of the lead screws, other electrical motors such as servo motors and the like, suitable for providing smooth controlled rotation and/or feedback to the controller, may be utilized without departing from the scope of the invention.

Referring to FIG. 1, the radiation beam analyzer is illustrated. The controller includes a hand control 72 having at least one manually operable member 74, e.g. switch, for instructing an input of a desired direction for manually controlled movement of an operator determined axis carriage. Within the preferred embodiment the controller includes a computer 76 electrically connected thereto for operational control of the axes movements, whereby the computer is constructed and arranged to accept commands from an operator to cause movement of the radiation detection probe under computer control throughout a predetermined field within a two or three-dimensional space. In response to the radiation measurements taken, the computer is constructed and arranged to produce a graphical representation 78 of the recorded density and distribution of the radiation beam associated with the scan.

Figure 13:
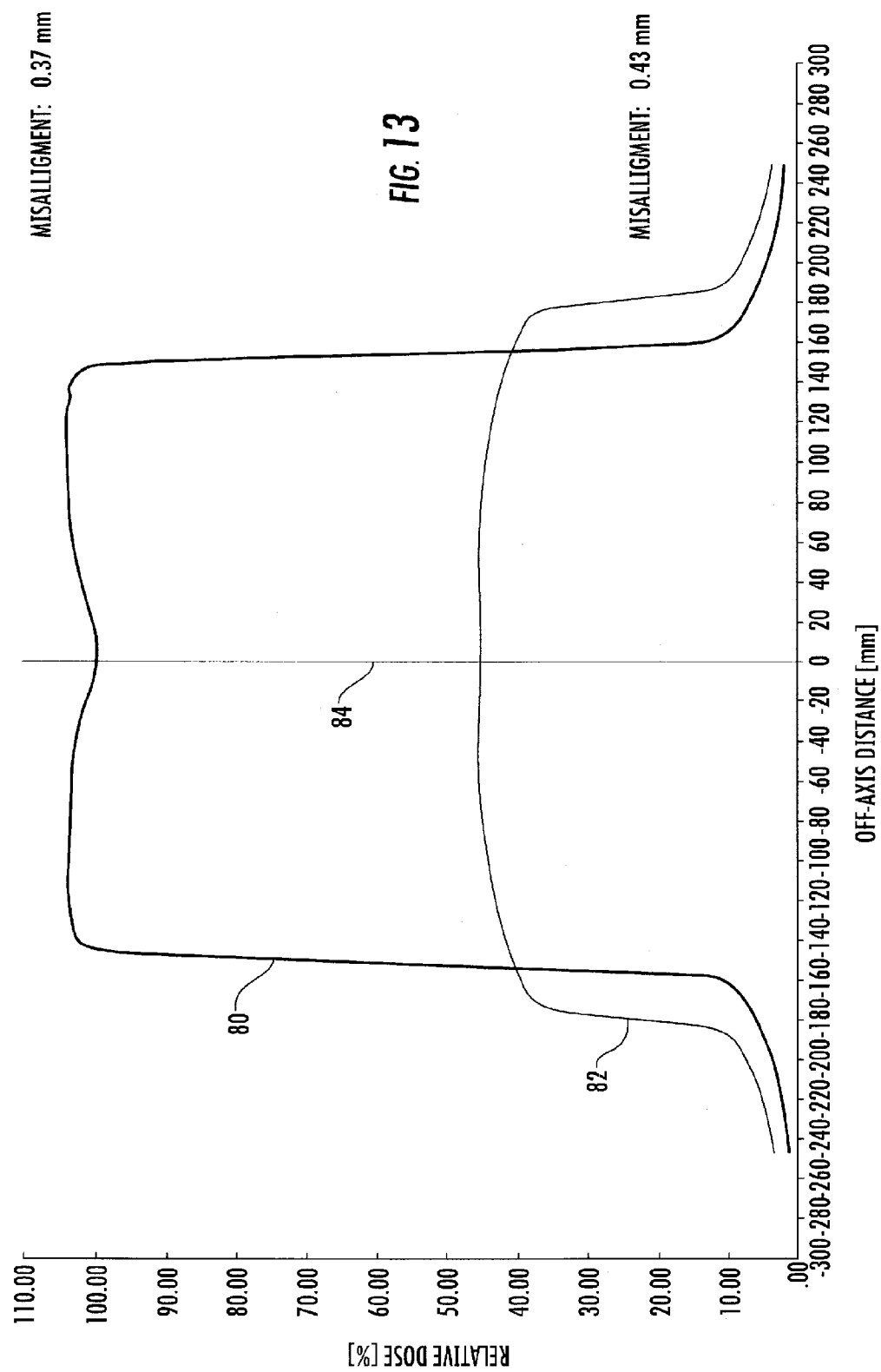
FIG. 13 is a graph illustrating a method of electronically leveling the radiation detection device of the instant invention.

Referring to FIG. 13 a graphical representation of an electronic leveling method is illustrated. In this embodiment, the computer is constructed and arranged to permit electronic leveling of the axes with respect to the top surface of the water within the phantom tank. To complete the electronic leveling, a scan having a large profile, about 30 cm×30 cm, is taken at a depth close to the surface of the water represented by line 80. The first scan is preferably taken at a depth referred to in the art as Dmax, or the depth at which the radiation is at the highest level within the phantom tank. Then a second scan of the same field size is taken at a depth close to the bottom of the phantom tank, about 30 cm, represented by line 82. The center of the radiation field is found for each scan 80 and 82. A theoretical line, represented by line 84, is drawn through the field centers. Because variations in water depth result in variations in radiation intensity, line 84 will be substantially perpendicular with respect to the upper surface of the water. The computer includes an algorithm that utilizes line 84 to create a datum plane substantially parallel with respect to the upper surface of the water. Thereafter the computer can manipulate movement of the axes to maintain the probe on a parallel course with respect to the datum plane and thus the upper surface of the water.

Figure 15:
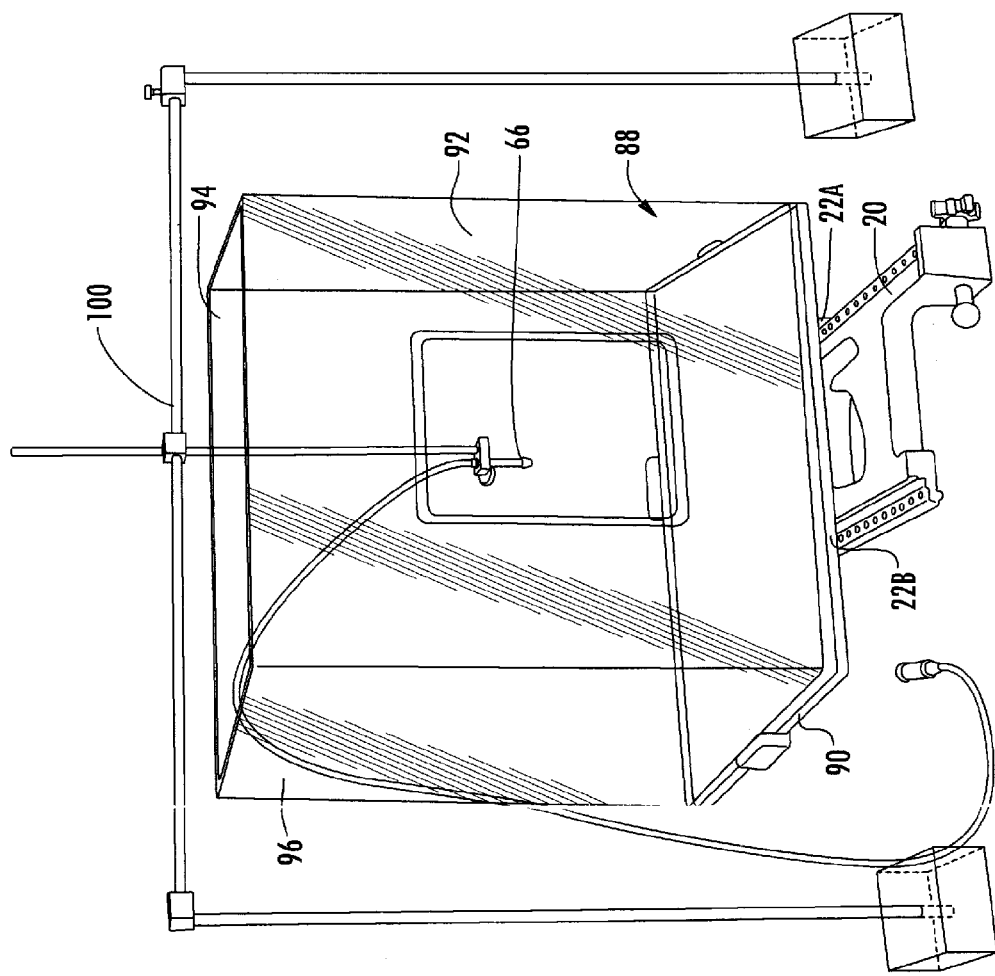
FIG. 15 is a perspective view illustrating the X-axis guideway of the instant invention in combination with a trapezoidal shaped tank for direct measurement of Tissue Maximum Ratio and/or Tissue Phantom Ratio.
Figure 16:
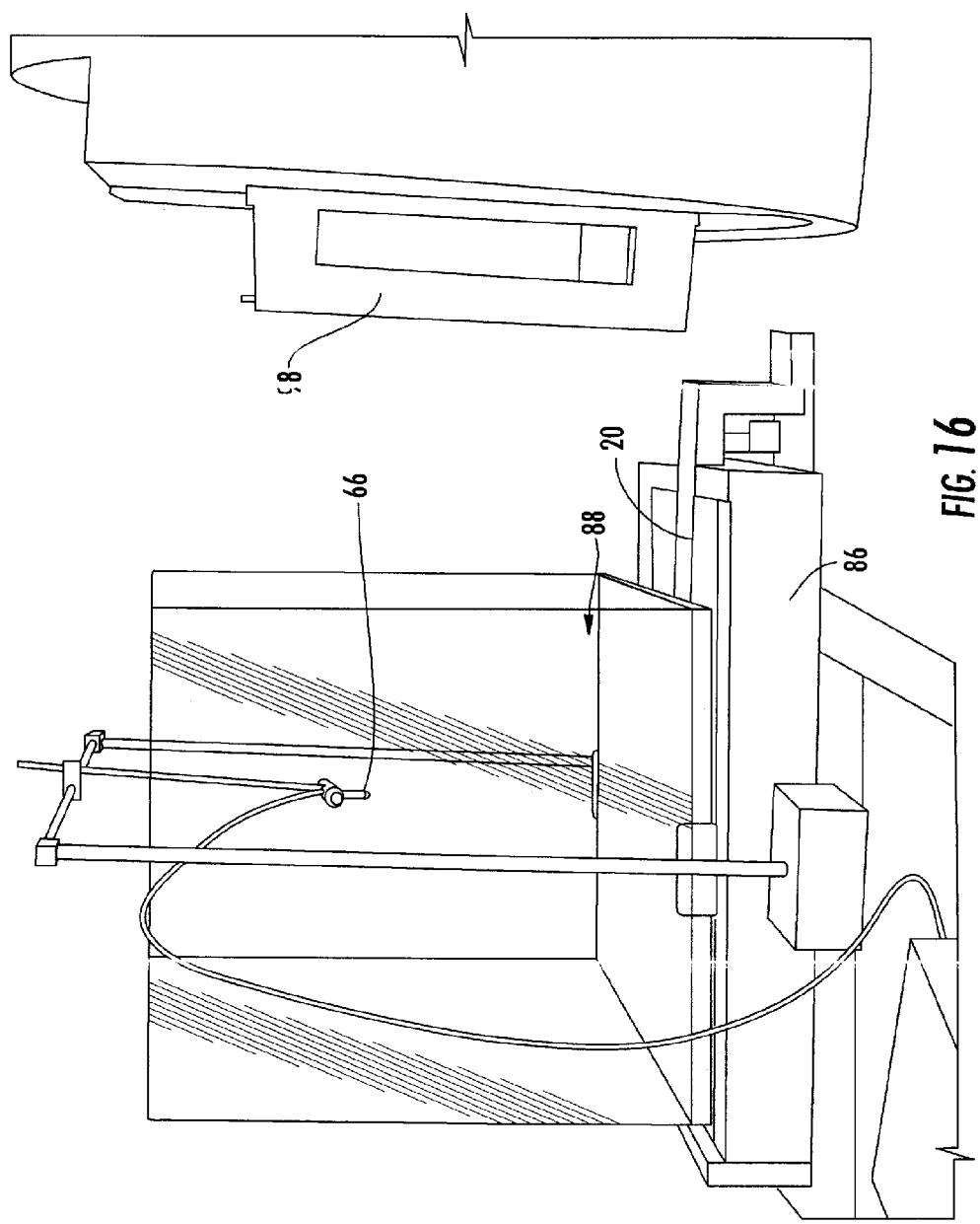
FIG. 16 is a perspective view illustrating operation of the embodiment shown in FIG. 15.

Referring to FIGS. 15 and 16, an alternative method of utilizing the X-axis module for direct measurement of Tissue Maximum Ratio (TMR) and/or Tissue Phantom Ratio (TPR) is illustrated. In this embodiment the X-axis module 20 is secured to a base member 86 in a oriented 90 degrees from the vertical as shown in FIG. 1. A trapezoidal water tank 88 is secured to the carriages 22A and 22B of the x-axis guideway 21 for movement therewith. The trapezoidal shaped tank has a base 90 and upstanding planar walls in a trapezoidal shape with a short wall 92, an opposite a long wall 94, and two connecting opposite side walls 96. The base and walls of the tank may be constructed of acrylic or other suitable material. The radiation detection probe 66 is secured in a fixed position with a suitable probe fixture 100. When filled with water, the tank 88 serves as a water phantom simulating the body of a patient undergoing radiation treatment. The trapezoidal shape reduces the amount of water necessary for the calibration and eliminates the need to pump water to and from the tank, as required by the prior art. In operation, the depth of the water phantom is unaffected but the radiation beam may be oriented 90 degrees from the vertical, as shown in FIG. 16, and the short wall 92 placed next to the radiation source 98 which aligns the horizontal dimensions of the water phantom with the broadening scatter of the beam. The tank is traversed along the X-axis guideway toward the radiation source and radiation level measurements are taken. The duration of the process taking about 1 minute.

Referring to FIG. 17, an alternative method of utilizing the X-axis module and the Y-axis module in combination with a dynamic phantom is illustrated. In this embodiment the X-axis module 20 is secured to a base member 86 in a oriented 90 degrees from the vertical as shown in FIG. 1. The Z-axis module 32 is secured to the X-axis module 20 for two-dimensional movement of a dynamic phantom 104. In operation, the dynamic phantom is moved throughout two axes and radiation level measurements are taken. The duration of the process taking about 1 minute. A more detailed description of dynamic phantoms and their applications can be found in U.S. Pat. No. 6,255,622, issued to the instant inventor, the contents of which are incorporated herein in their entirety.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A modular radiation beam analyzer for measuring the distribution and intensity of radiation produced by a radiation source comprising:
a phantom tank constructed and arranged to contain a material having a density approximating that of a human body, said phantom tank sized to accommodate an X-axis module, a Y-axis module and a Z-axis module of said radiation beam analyzer;
said X-axis module including an X-axis guideway extending substantially across an upper portion of said phantom tank, including an X-axis carriage slidably secured to said X-axis guideway for controlled movement along the length thereof;
said Z-axis module including a Z-axis guideway, said Z-axis guideway secured to said X-axis carriage for movement therewith, including a Z-axis carriage slidably secured to said Z-axis guideway for controlled movement along the length thereof;
said Y-axis module including a Y-axis beam member, said Y-axis beam member secured to said Z-axis carriage for movement therewith;
at least one radiation detection probe secured to said Y-axis beam member, said radiation detection probe constructed and arranged to sense photons and electrons;
a controller electrically connected to said X-axis and said Z-axis for providing electrical signals thereto, whereby said controller includes a manually operable member for instructing an input of a desired direction for manually controlled movement of said X and Z axes carriages, whereby movement of said dosimetry probe through a volumetric space provides data to determine radiation density and distribution of a radiation beam.

2. The modular radiation beam analyzer of claim 1 wherein said Y-axis beam member is constructed and arranged for infinite manual positioning of said dosimetry probe along the length of said Y-axis beam member.

3. The modular radiation beam analyzer of claim 1 wherein said X-axis guideway includes a first lead screw rotatably mounted thereon, said first lead screw operably connected to said X-axis carriage to provide linear motion thereto during rotation of said first lead screw, a first stepper motor operably connected to said first lead screw for controlled bi-directional rotation thereof, said first stepper motor in electrical communication with said controller;
wherein said Z-axis guideway includes a third lead screw rotatably mounted thereon, said third lead screw operably connected to said Z-axis carriage to provide linear motion thereto during rotation of said third lead screw, a third stepper motor operably connected to said third lead screw for controlled bi-directional rotation thereof, said third stepper motor in electrical communication with said controller.

4. The modular radiation beam analyzer of claim 1 wherein said Y-axis includes a Y-axis guideway, said Y-axis guideway secured to said Z-axis carriage for movement therewith, a Y-axis carriage slidably secured to said Y-axis guideway for controlled movement along the length thereof, said at least one dosimetry probe secured to said Y-axis carriage for movement therewith, wherein said controller is electrically connected to said Y-axis for providing electrical signals thereto, whereby said controller includes a manually operable member for instructing an input of a desired direction for manually controlled movement of said y axis carriage, whereby movement of said dosimetry probe through a three dimensional volumetric space provides data to determine radiation density and distribution.

5. The modular radiation beam analyzer of claim 4 wherein said Y-axis guideway includes a second lead screw rotatably mounted thereon, said second lead screw operably connected to said Y-axis carriage to provide linear motion thereto during rotation of said second lead screw, a second stepper motor operably connected to said second lead screw for controlled bi-directional rotation thereof, said second stepper motor in electrical communication with said controller.

6. The modular radiation beam analyzer of claim 4 wherein said Z-axis guideway includes a line-shaft rotatably secured thereon, said line-shaft operably connected to a second stepper motor for selective bi-directional rotation thereof, said second stepper motor in electrical communication with said controller, said line-shaft operably connected to said second lead screw to provide rotational motion thereto, whereby rotation of said line-shaft causes rotation of said second lead screw to cause movement of said Y-axis carriage.

7. The modular radiation beam analyzer of claim 6 wherein said line-shaft includes at least one spline extending substantially along the length thereof, a first bevel gear slidably mounted on said line-shaft for movement with said Z-axis carriage, whereby said at least first bevel gear is constructed and arranged to operably engage said second lead screw.

8. The modular radiation beam analyzer of claim 4 wherein said controller includes a computer for operational control of said first stepper motor, said second stepper motor and said third stepper motor, whereby said computer is constructed and arranged to accept commands from an operator to cause movement of said dosimetry probe under computer control throughout a predetermined field within said three-dimensional space.

9. The modular radiation beam analyzer of claim 8 wherein said computer is constructed and arranged to produce a graphical representation of said recorded density and distribution of said radiation beam associated with said relative position.

10. The modular radiation beam analyzer of claim 9 wherein said computer is constructed and arranged to produce a graphical representation of said recorded density and distribution of said radiation beam associated with said relative position.

11. The modular radiation beam analyzer of claim 4 wherein said dosimetry probe is an ion chamber.

12. The modular radiation beam analyzer of claim 4 wherein said radiation beam is generated by a linear accelerator.

13. The modular radiation beam analyzer of claim 4 wherein said radiation beam is generated by a cobalt radiation machine.

14. The modular radiation beam analyzer of claim 1 wherein said controller includes a computer for operational control of said first stepper motor and said third stepper motor, whereby said computer is constructed and arranged to accept commands from an operator to cause movement of said dosimetry probe under computer control throughout a predetermined field within said two-dimensional space.

15. The modular radiation beam analyzer of claim 14 wherein said computer is constructed and arranged to measure and record the relative position of said dosimetry probe as well as said density and distribution of said radiation beam associated with said relative position.

16. The modular radiation beam analyzer of claim 15 wherein said computer is constructed and arranged to produce a graphical representation of said recorded density and distribution of said radiation beam associated with said relative position.

17. The modular radiation beam analyzer of claim 1 wherein said dosimetry probe is an ion chamber.

18. The modular radiation beam analyzer of claim 1 wherein said radiation beam is generated by a linear accelerator.

19. The modular radiation beam analyzer of claim 1 wherein said radiation beam is generated by a cobalt radiation machine.

20. A method of electronically leveling a radiation beam analyzer probe with respect to the top surface of water contained within a phantom tank comprising the steps of:
    scanning a first profile of a radiation beam at a depth substantially at said top surface of said water contained within said phantom tank;
    scanning a second profile of said radiation beam at a depth substantially close to the bottom surface of said phantom tank;
    determining a center point of the radiation field for said first scan;
    determining a center point of the radiation field for said second scan;
    connecting said center point of said first scan with said center point of said second scan to create a datum line, whereby said datum line is substantially perpendicular with respect to said top surface of said water contained within said phantom water tank;
    inputting said datum line into an algorithm to create a reference datum plane, whereby said datum plane is substantially parallel to said top surface of said top surface of said water contained within said phantom water tank;
    manipulating movement of said probe to maintain a substantially parallel course with respect to said datum plane.

21. A method of measuring Tissue Maximum Ratio radiation comprising the steps of:
    providing an X-axis module including an X-axis guideway having an X-axis carriage slidably secured to said X-axis guideway for controlled movement along the length thereof;
    securing a trapezoidal shaped water phantom tank to said X-axis guideway for movement therewith;
    securing a radiation detection probe at a predetermined position within said tank so that said tank will move along said X-axis without substantial movement of said probe;
    filling said tank with a material having a density approximating that of a human body;
    orienting a radiation beam so that the broadening scatter of said radiation beam aligns with the dimensions of said tank;
    traversing the tank along said X-axis guideway toward a source of said radiation beam while taking radiation level measurements with said radiation detection probe.

22. A method of measuring the distribution and intensity of radiation produced by a radiation source comprising the steps of:
    providing an X-axis module including an X-axis guideway having an X-axis carriage slidably secured to said X-axis guideway for controlled movement along the length thereof;
    securing a Z-axis module to said X-axis carriage for movement therewith, said Z-axis module having a Z-axis guideway, a Z-axis carriage slidably secured to said Z-axis guideway for controlled movement along the length thereof;
    securing a dynamic phantom to said Z-axis carriage for movement therewith;
    traversing said dynamic phantom throughout a predetermined two dimensional path whereby said dynamic phantom passes through a radiation beam;
    recording a plurality of radiation measurements as said dynamic phantom passes through said radiation beam.

* * * * *